United States Patent [19]
Phillips

[11] Patent Number: 5,996,586
[45] Date of Patent: Dec. 7, 1999

[54] BREATH TEST FOR DETECTION OF LUNG CANCER

[76] Inventor: Michael Phillips, 1 Horizon Rd., Fort Lee, N.J. 07024

[21] Appl. No.: 08/951,884

[22] Filed: Oct. 16, 1997

Related U.S. Application Data

[60] Provisional application No. 60/041,380, Mar. 26, 1997, abandoned.

[51] Int. Cl.$^6$ ........................................... A61B 19/00
[52] U.S. Cl. ..................... 128/898; 436/64; 128/206.29
[58] Field of Search .............................. 128/898, 206.29, 128/204.17; 600/532, 543, 473; 436/64, 900, 96, 813

[56] References Cited

U.S. PATENT DOCUMENTS

| | | | |
|---|---|---|---|
| 4,534,360 | 8/1985 | Williams | 600/473 |
| 4,772,559 | 9/1988 | Preti et al. | 436/64 |
| 5,465,728 | 11/1995 | Phillips | 600/543 |

*Primary Examiner*—Mickey Yu
*Assistant Examiner*—Kelly O'Hara
*Attorney, Agent, or Firm*—Kane, Dalsimer, Sullivan and Levy, LLP

[57] ABSTRACT

A method of detecting and diagnosing the probable presence of lung cancer in a mammal, including a human, comprising collecting a measured quantity of alveolar breath from the mammal; analyzing the collected breath for the presence of a marker for lung cancer; determining a first mean alveolar gradient for the marker present in the mammal's breath; comparing the first mean alveolar gradient for the marker present in the mammal's breath to a second mean alveolar gradient for the same marker, found in the breath of a mammal free of lung cancer.

1 Claim, 2 Drawing Sheets

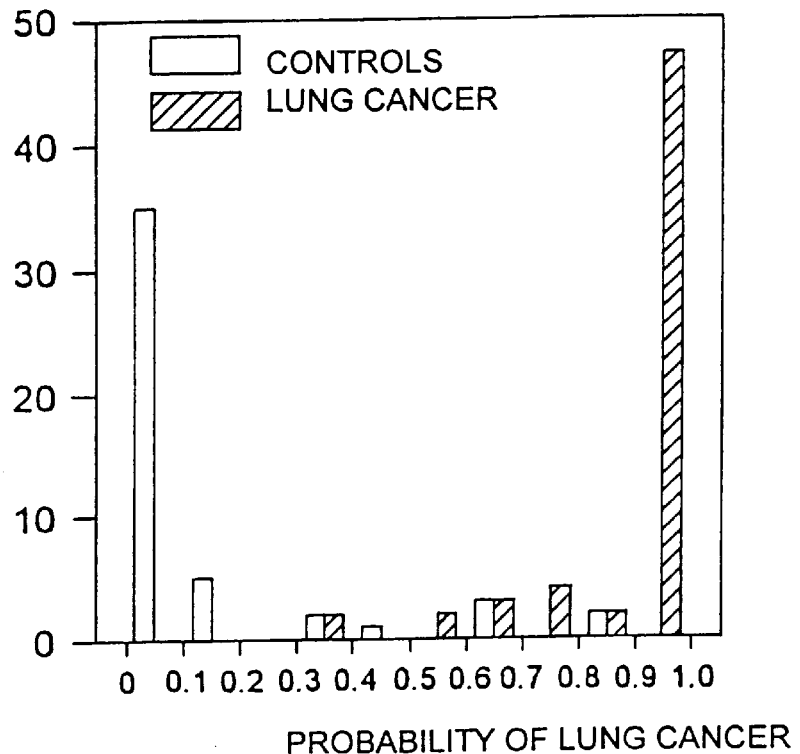
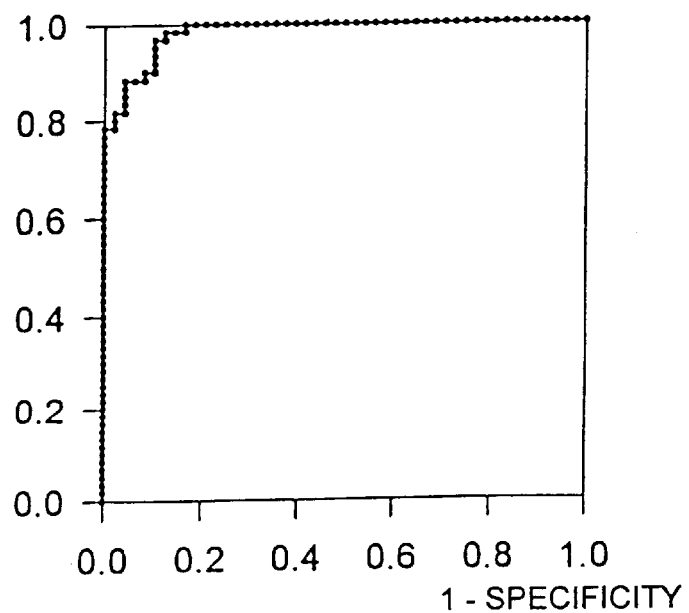
F I G. 1

BREATH TEST FOR DETECTION OF LUNG CANCER

CROSS-REFERENCE TO RELATED APPLICATION

This application claims the priority of Provisional Application Ser. No. 60/041,380 filed Mar. 26, 1997 now abandoned.

BACKGROUND OF THE INVENTION

1. Field of the Invention

The invention relates to methods of detecting and diagnosing lung cancers in mammals.

2. Brief Description of Related Art

Primary carcinoma of the lung is the leading cause of cancer death in the United States. Every year, more than 100,000 males and 50,000 females develop lung cancer, and most of them die within twelve months. There is a clinical need for a screening test which can detect lung cancer in its earliest stages because prompt treatment of localized disease improves the 5-year survival rate to 30% in males and 50% in females. However, most cases are not detected until local or metastatic growth causes symptoms, and prospective screening with frequent radiography and sputum cytology has not improved the survival rate in smoking males aged 45 years or older. Since early detection of lung cancer can potentially reduce mortality, researchers have investigated alternative diagnostic technologies such as breath testing.

The rationale of a breath test for lung cancer is based upon three observations: first, carcinogenesis is accompanied by increased production of oxygen free radicals (OFRs), second, OFRs degrade cell membranes by lipid peroxidation, evolving alkanes such as ethane and pentane, and third, these alkanes are volatile organic compounds (VOCs) which are excreted in the breath.

OFRs cause mutagenesis by oxidative damage to DNA; as a result, affected cells acquire malignant properties and tumor clones expand. The mutagenic effects of OFRs appear to be partially reversible; treatment with OFR scavengers significantly improved survival in metastatic gastric cancer as well as in a rat model of colon cancer induced by 1,2-dimethylhydrazine. Oxidative stress has also been associated with chemical toxicity, ischemia, inflammation and dietary deficiency of antioxidants. The final common pathway is the intracellular accumulation of OFRs which overcome cellular defense mechanisms and degrade cellular membranes by lipid peroxidation, resulting in chemical and anatomical disruption of the membranes which may progress to cell death.

Breath hydrocarbons, particularly alkanes such as pentane, are markers of oxidative stress mediated by OFRs. Increased breath pentane has been reported in breast cancer, acute myocardial infarction, heart transplant rejection, rheumatoid arthritis, and acute bronchial asthma. Previous studies have attempted to identify the VOCs in breath which might provide clinically useful markers of lung cancer. Gordon et al reported 28 VOCs which were present in the breath of more than 90% of patients with lung cancer; and Preti et al found increased o-toluidine;

Preti G, Labows J N, Kostelc J G and Aldinger S: Analysis of lung air from patients with bronchogenic carcinoma and controls using gas chromatography mass spectrometry. J. Chromatography 1988;432:1–11.

Gordon S M, Szidon J P, Krotoszynski B K, Gibbons R D and O'Neill H J:

Volatile organic compounds in exhaled air from patients with lung cancer. Clin Chem 1985; 31:1278–82;

O'Neill H J, Gordon S M, O'Neill M H, Gibbons R D and Szidon J P: A computerized classification technique for screening for the presence of breath biomarkers in lung cancer. Clin Chem 1988; 34(8):1613–1618.

However, progress in breath testing for lung cancer has been impeded by the technical difficulty of detecting VOCs in breath. The majority are excreted in very low concentrations: nanomolar ($10^{-9}$ mol/l) or picomolar ($10^{-12}$ mol/l). Most existing laboratory instruments cannot detect VOCs in such low levels in breath unless the sample is concentrated prior to analysis. Researchers have circumvented this problem by constructing specialized instruments for the collection and concentration of breath samples. Phillips has recently described a method for the collection and analysis of breath VOC samples which can be employed in clinical settings. A portable microprocessor-controlled breath collection apparatus collects alveolar breath VOCs onto sorbent traps which are then analyzed by conventional gas chromatography and mass spectroscopy. This breath collection apparatus was utilized to collect samples from patients undergoing bronchoscopy and biopsy for suspected lung cancer, in order to correlate the VOCs in alveolar breath with the histopathologic screening tests.

Phillips M: Method for the collection and assay of volatile organic compounds in breath. Analytical Biochemistry 1997;247:272–278.

SUMMARY OF THE INVENTION

The invention comprises a method of detecting and diagnosing lung cancer in a mammal, including a human, which comprises;

collecting a measured quantity of alveolar breath from the mammal; and analyzing the collected breath for the presence of a hydrocarbon marker for lung cancer;

the detection of the hydrocarbon markers being indicative of the presence of a lung cancer screening test.

The test method is simple, non-invasive and economical as a screening test procedure.

BRIEF DESCRIPTION OF THE DRAWINGS

FIG. 1: Results of breath testing in patients with and without lung cancer. The left-hand panel show posterior probability of disease as determined by logistic regression analysis of alveolar gradients of significant VOCs in breath (identified in Table 2). The right-hand panel demonstrates the receiver operating characteristic (ROC) curve of diagnostic sensitivity and specificity of this model.

DETAILED DESCRIPTION OF THE INVENTION

Figure 2:
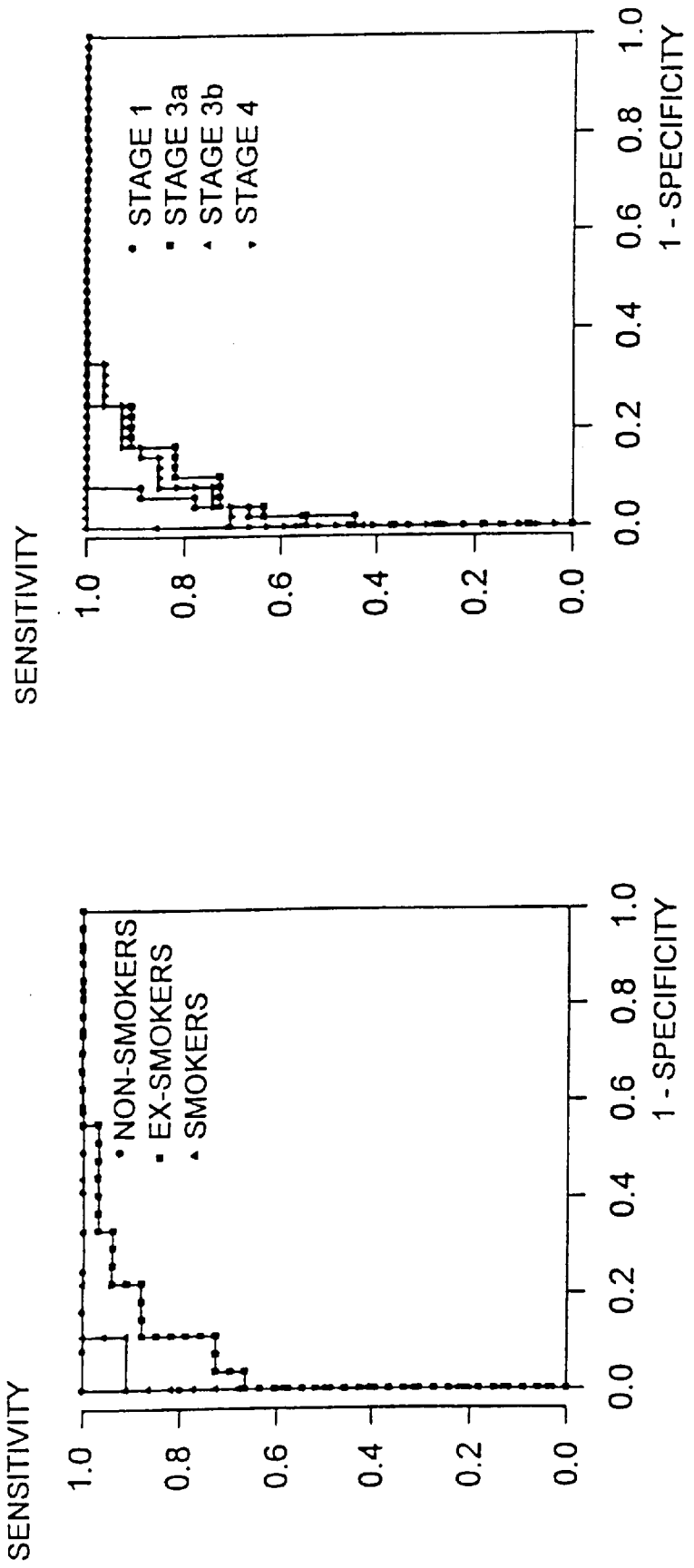
FIG. 2: Performance of the breath test in subgroups. ROC curves demonstrate the sensitivity and specificity of the test according to smoking behavior, stage of the lung cancer, adenocarcinoma versus epidermoid carcinoma, small cell versus non-small cell carcinoma, age and sex.

Breath VOC analysis is a non-invasive procedure which opens a window onto the composition of the VOCs circulating in the blood. Like water flowing down a hill, VOCs flow down the concentration gradient from blood into breath (or vice versa) by rapid diffusion across the pulmonary alveolar membrane. Breath tests are potentially more sensitive than blood tests because the quantity of collected analyte is limited only by the capacity of the breath collection apparatus and the patience of the donor. Breath testing was pioneered in the eighteenth century by Lavoisier; his discovery that humans and animals excrete carbon dioxide in their breath was the first evidence for oxidative metabolism of foodstuffs. Nineteenth century researchers reported breath tests for ethanol and for elevated acetone in uncontrolled diabetes mellitus. The modern era of breath testing dates from 1971, when Linus Pauling and his colleagues discovered that a sample of concentrated human breath contained several hundred VOCs when analyzed by gas chromatography.

Alveolar gradients of a number of the VOCs in Table 2 (below) were significantly lower or more negative in the cancer patients than in the controls. This apparently paradoxical finding is consistent with the observations of Khyshiktuev et al, who also detected a reduction in breath markers of lipid peroxidation in patients with lung cancer. The simplest hypothesis which might account for these findings is that lung cancer is associated with an increased rate of metabolism and/or excretion of alkanes and their derivatives. Breath VOCs excreted in vivo are the product of a number of interacting kinetic processes: absorption, distribution, metabolism (anabolism and catabolism) and excretion. Hence, alkanes produced in the lung by cancer cells may be catabolized and excreted in the lung or at other sites. Pentane is metabolized in vivo by the cytochrome P-450 system, a pathway which can be induced by phenobarbital and inhibited by cimetidine. Radiolabelled ethane and pentane are both metabolized to $CO_2$. Several studies have confirmed increased cytochrome P450 activity in cancer, which is known to cause carcinogen activation and correspondingly increased cancer risk in animal models. Drugs such as phenobarbital which induce increased cytochrome P450 activity also induce hepatic carcinogenesis in animals.

Since the number of breath VOCs exceeded the number of subjects, there is a risk that some of the VOCs in Table 2 may have been selected as markers of lung cancer by chance alone. However, this is not likely for at least three reasons:

First, there is the internal evidence of structural clustering of VOCs. Several of the VOCs were structurally similar to one another e.g. eight were derivatives of cyclohexane, four of nonane, three each of heptane, pentane and hexane. This is unlikely to have occurred by chance, and is consistent with an abnormality in alkane metabolism resulting in altered production of a number of closely related compounds in the same metabolic pathway.

Second, the majority of the significant VOCs in patients with lung cancer were either methylated alkanes or their derivatives, which is consistent with the hypothesis that they represent lipid peroxidation products of OFR activity. VOCs were predominantly derivatives of ethane, propane, pentane, hexane, heptane, octane and nonane.

Third, nine of the significant VOCs in patients were similar to those reported by Gordon et al as markers of lung cancer (O'Neil, H. J., et al. supra.) with comparatively minor differences in chemical structure which may be attributable to the use of different libraries of mass spectra. An isoprenoid breath VOC reported by O'Neill et al as a possible shunt pathway in sterol metabolism, 1-methyl-4-(1-methylethenyl) cyclohexene was also identified as a significant VOC in patients with lung cancer.

We conclude that breath VOC analysis is a non-invasive test which detect lung cancer with high sensitivity and specificity. If these findings are confirmed in validation studies, breath testing might be employed as a new screening test to identify patients with early stage lung cancer, and potentially improve their prospects of survival.

Human subjects: Breath samples were collected from patients prior to bronchoscopy in the pulmonary medicine services of two academic medical centers: Penn State Medical Center (the Milton S Hershey Medical Center, Hershey, Pa.) and the Royal Postgraduate Medical School (London, England). Patients were included if they were aged over 18, able to understand the breath collection procedure, give signed informed consent, and were scheduled for bronchoscopy for evaluation of a suspicious x-ray in order to confirm or exclude lung cancer. A "suspicious x-ray" was defined as the presence of a lung mass, or a lung infiltrate with volume loss suggestive of endobronchial tumor. Patients were excluded if previous investigations had confirmed a neoplasm of the lung or of some other site. The research was approved by the institutional review boards of all participating institutions.

Bronchoscopy and biopsy: Bronchoscopy was performed according to standard procedures. Following premedication with intramuscular meperidine and atropine, the patient's nose, nasopharynx, and oropharynx was sprayed with a 1% lidocaine solution. The bronchoscope was then passed through the most patent nare through the upper airway and into the tracheo-bronchial tree. Intraluminal lesions were ravaged or brushed for cytology, and directly biopsied using a standard alligator forceps. Parenchymal lesions were evaluated by lavage of the appropriate airway segment and by transbronchial biopsy under direct fluoroscopic guidance. Lung biopsy specimens were preserved in formalin for microscopic examination by a pathologist.

Collection of breath VOCs: The method has been described (Phillips, M., supra). A portable breath collecting apparatus as described in U.S. Pat. No. 5,465,728, incorporated herein by reference thereto was employed to collect breath VOCs onto sorbent traps. Subjects sat in front of the apparatus wearing a nose clip, breathing in and out through a disposable mouthpiece. Alveolar breath was sampled at 2.0 liters/min for 5.0 min and drawn through a sorbent trap which captured the VOCs. A sample of ambient room air was collected in a similar fashion onto another sorbent trap. Traps were stored in hermetically sealed containers in order to prevent sample loss or contamination.

Analysis of breath VOCs: The method has been described (Phillips, M., supra). Using automated instrumentation, breath VOCs were thermally desorbed from the sorbent trap, concentrated by two-stage cryofocusing, separated by gas chromatography, then quantified and identified by mass spectroscopy. A typical chromatogram of an alveolar breath sample yielded 150–250 different VOCs, all of which were automatically identified and quantified. The chemical structure of each VOC was tentatively identified from its mass spectrum, utilizing a computer-based library. Each VOC was quantified by measuring the area under curve (AUC) of the chromatographic peak, and calculating the ratio of the AUC to the AUC of a standard.

Blinding procedures: The breath samples were analyzed without knowledge of the bronchoscopy or biopsy findings. Neither the physicians who performed the bronchoscopies nor the pathologists who evaluated the biopsy specimens had any knowledge of the results of the breath test.

Analysis of data: The alveolar gradient of each VOC was determined as the concentration in alveolar breath minus the concentration in inspired air i.e. alveolar gradient=$AUC_{VOC\ in\ breath}/AUC_{standard} - AUC_{VOC\ in\ air}/AUC_{standard}$. The alveolar gradients of all VOCs detected in at least three breath samples were compared in subjects with and without lung cancer. Since the number of variables (breath VOCs) exceeded the number of subjects, alveolar gradients were screened first by Student's test and then by factor analysis. Significant VOCs (p<=0.05) were subjected to a principal component analysis with varimax rotation, using the Kaiser criterion of limiting the number of factors to those possessing an eigenvalue greater than one. Factor scores were analyzed by logistic regression (logit) in order to determine the posterior probability of lung cancer in each subject from which the sensitivity and specificity of the breath test was derived.

RESULTS

Human subjects: 108 subjects were studied and none experienced any adverse effects of the breath test. Lung cancer was confirmed histologically in 60 and excluded in 48. Characteristics of the subjects and their screening tests are shown in Table 1, below.

TABLE 1

|  | Hershey | London | Total |
|---|---|---|---|
| Number of patients | 73 | 35 | 108 |
| Sex (M/F) | 43/30 | 20/15 | 108 |
| Smoking status: |  |  |  |
| non-smoker | 13 | 4 | 17 |
| smoker | 17 | 14 | 31 |
| ex-smoker | 43 | 17 | 60 |
| Age:mean(SD) | 63.6(12.1) | 65.7(15.3) | 64.3(13.2)NS |
| Cancer type small cell | 7 | 3 | 10 |
| non-small cell: all | 30 | 20 | 50 |

TABLE 1-continued

|  | Hershey | London | Total |
|---|---|---|---|
| epidermoid | 12 | 12 | 24 |
| adenocarcinoma | 15 | 8 | 23 |
| large cell | 1 | 0 | 1 |
| mesothelioma | 1 | 0 | 1 |
| melanoma 1 | 0 | 1 |  |
| Stage of cancer |  |  |  |
| 0 | 36 | 12 | 48 |
| X | 2 | 1 | 3 |
| I | 4 | 5 | 9 |
| II | 2 | 1 | 3 |
| IIIa | 5 | 6 | 11 |
| IIIb | 6 | 1 | 7 |
| IV | 18 | 9 | 27 |

Breath VOC Analysis: 1124 different VOCs were observed in three or more samples of alveolar breath. The mean alveolar gradients of 44 VOCs, predominantly methylated alkanes, were significantly different in subjects with lung cancer (Table 2 below). The posterior probability of lung cancer in patients with and without disease, and the receiver operating characteristic (ROC) curve of sensitivity and specificity of the breath test are shown in FIG. 1. At the shoulder of the curve, the test exhibited 93.3% sensitivity and 91.7% specificity. With 100% sensitivity, the test was 75.0% specific; with 100% specificity, the test was 88.3% sensitive. The sensitivity and specificity of the test in subgroups is shown in FIG. 2, in ROC curves for smoking status, stage of cancer, cancer cell type (epidermoid versus adenocarcinoma, small-cell versus non small-cell carcinoma), age and sex.

TABLE 2

|  | MEAN ALVEOLAR GRADIENT (SD) | | | | | |
|---|---|---|---|---|---|---|
|  | Controls | | Lung Cancer | | mean difference | |
| 2-heptanone | −6.716 | (12.057) | −0.948 | (3.167) | 5.768 | p < 0.001 |
| nonane, 4-methyl- | 2.876 | (11.306) | −4.121 | (10.833) | −6.997 | p < 0.01 |
| heptanal | −59.366 | (75.299) | −26.970 | (30.715) | 32.396 | p < 0.01 |
| nonane, 2-methyl- | 1.423 | (10.973) | −3.825 | (9.652) | −5.247 | p < 0.01 |
| 1,1'-bicyclopentyl | 1.621 | (4.307) | 0.019 | (0.92) | −1.602 | p < 0.01 |
| nonane | 11.507 | (68.481) | −19.132 | (44.724) | −30.639 | p < 0.01 |
| octane, 4-methyl- | 3.181 | (9.101) | −4.004 | (16.633) | −7.185 | p < 0.01 |
| hexanal | −84.459 | (103.576) | −44.113 | (54.317) | 40.346 | p < 0.05 |
| cyclohexane, propyl- | 3.064 | (21.328) | −5.096 | (10.924) | −8.160 | p < 0.05 |
| acetonitrile, trideutero | 926.172 | (2814.177) | −1.789 | (33.658) | −927.961 | p < 0.05 |
| 2-hexanamine, 5-methyl- | −0.183 | (0.899) | 2.722 | (8.137) | 2.905 | p < 0.05 |
| cyclopropane, 1-butyl-2-methyl, cis | 0.255 | (3.862) | −1.935 | (5.217) | −2.190 | p < 0.05 |
| cyclohexane, 1,1,3-trimethyl- | 2.999 | (11.931) | −1.168 | (6.044) | −4.167 | p < 0.05 |
| ethane, 2-chloro-1-(difluoromethoxy)-1,1,2-trifluoro- | −7.610 | (73.872) | −58.523 | (134.692) | −50.913 | p < 0.05 |
| heptane, 3-ethyl-2-methyl- | −0.295 | (4.309) | −4.083 | (10.503) | −3.788 | p < 0.05 |
| cyclohexane, 1,3-dimethyl-, trans- | 4.981 | (19.095) | −2.146 | (12.96) | −7.127 | p < 0.05 |
| 1-propene, 3-(methylthio)- | 7.120 | (22.093) | 0.276 | (6.627) | −6.844 | p < 0.05 |
| octane, 3,6-dimelhyl- | 3.098 | (18.295) | −4.224 | (15.149) | −7.322 | p < 0.05 |
| pentane, 2,3-dimethyl- | 18.788 | (68.865) | −2.163 | (16.922) | −20.951 | p < 0.05 |
| chloroform | −7.895 | (18.108) | −0.861 | (14.235) | 7.034 | p < 0.05 |
| ethanone, 1-(1-methyl-2-cyclopenten-1-yl)- | 0.124 | (0.862) | 1.346 | (3.806) | 1.222 | p < 0.05 |
| acetamide, 2-cyano- | −0.770 | (3.3) | 2.199 | (8.972) | 2.969 | p < 0.05 |
| 4-(1,1-dimethylethyl)-cyclohexene | −0.408 | (1.456) | 0.000 | (0.000) | 0.408 | p < 0.05 |
| cyclohexene, 1-methyl-4-(1-methytethenyl)-, (R)- | 251.320 | (745.687) | −48.775 | (705.573) | −300.095 | p < 0.05 |
| cyclopropane, 1,1-dimethyl- | −1.148 | (5.134) | 0.409 | (2.100) | 1.557 | p < 0.05 |
| ethanol, 2-methoxy-, acetate | −5.859 | (21.128) | −0.044 | (0.338) | 5.815 | p < 0.05 |
| hydrazine, 1-methyl-1-(1-methylethyl) | 0.272 | (0.992) | 0.000 | (0.000) | −0.272 | p < 0.05 |
| naphthalene, trans-anti-1-methyl-decahydro | −0.276 | (1.517) | −1.627 | (4.194) | −1.351 | p < 0.05 |
| benzene, ethynyl- | 0.542 | (3.771) | −0.700 | (2.264) | −1.242 | p < 0.05 |
| 2-methylbutylidene-cyclopentane | −0.260 | (0.881) | −0.017 | (0.130) | 0.243 | p < 0.05 |
| 4,7-ethano-1H-indene, octahydro | 0.614 | (2.037) | 0.051 | (0.399) | −0.563 | p < 0.05 |

TABLE 2-continued

| | MEAN ALVEOLAR GRADIENT (SD) | | | | | |
|---|---|---|---|---|---|---|
| | Controls | | Lung Cancer | | mean difference | |
| hexane, 5-methoxy-1-aza-6-oxabicyclo(3.1.0) | −0.753 | (2.945) | 0.640 | (3.821) | 1.393 | $p < 0.05$ |
| 1,1-dimethyl-cyclohexane | 0.725 | (3.069) | −0.101 | (0.459) | −0.826 | $p < 0.05$ |
| heptane, 4-(1-methylethyl)- | −0.520 | (2.26) | 0.171 | (1.197) | 0.691 | $p < 0.05$ |
| cyclohexane, 1,4-dimethyl-, -cis | −1.809 | (6.892) | 1.018 | (7.467) | 2.827 | $p < 0.05$ |
| pentanal | −9.370 | (18.676) | −1.215 | (22.549) | 8.155 | $p < 0.05$ |
| nonane, 3-methyl- | −1.565 | (25.328) | −11.251 | (24.577) | −9.686 | $p < 0.05$ |
| cydohexane, 1,2.3-trimethyl-, (1.alpha.,2.beta.,3.alpha.)- | 2.481 | (9.72) | −0.118 | (2.256) | −2.599 | $p < 0.05$ |
| pinene 2-beta- | 20.597 | (65.835) | 1.990 | (25.935) | −18.607 | $p < 0.05$ |
| [10B]-Triethylborane | 0.091 | (0.444) | −0.049 | (0.278) | −0.140 | $p < 0.05$ |
| piperazine, 2,5-dimethyl-, cis- | 0.000 | (0.000) | −0.697 | (2.421) | −0.697 | $p < 0.05$ |
| delta-4-carene | 0.461 | (2.438) | −0.550 | (2.828) | −1.011 | $p = 0.05$ |
| propanoic acid, 2-methyl-, 2-methylbutyl ester | −0.874 | (3.867) | 0.283 | (2.189) | 1.157 | $p = 0.05$ |
| pentane, 3-methyl- | −13.982 | (79.025) | −52.101 | (116.068) | −38.119 | $p = 0.05$ |

What is claimed is:

1. A method of detecting and diagnosing the probable presence of lung cancer in a mammal, including a human, which comprises;

collecting a measured quantity of alveolar breath from the mammal;

analyzing the collected breath for the presence of a marker for lung cancer;

said marker being a chemical compound selected from the group consisting of 2-heptanone,
4-methyl-nonane,
heptanal,
2-methyl-nonane,
1,1'-bicyclopentyl,
nonane,
4-methyl-octane,
hexanal,
propyl-cyclohexane,
trideuteroacetonitrile,
5-methyl-2-hexanamine,
1-butyl-2methyl, cis-cyclopropane,
1,1,3-trimethyl-cyclohexane,
2-chloro-1-(difluoromethoxy)-1,1,2-trifluoro-ethane,
3-ethyl-2-methy-heptane,
1,3-dimethyl-, trans-cyclohexane,
3-(methylthio)-1-propene,
3,6-dimethyl-octane,
2,3-dimethyl-pentane,
chloroform,
1-(1-methyl-2-cyclopenten-1-yl)-ethanone,
2-cyano-acetamide,
4-(1,1-dimethylethyl)-cyclohexene,
1-methyl-4-(1-methylethenyl)-, (R)-cyclohexene,
1,1-dimethyl-cyclopropane,
2-methoxy-ethyl, acetate,
1-methyl-1-(1-methylethyl)hydrazine,
trans-anti-1-methyl-decahydronaphthalene,
ethynyl-benzene,
2-methylbutylidene-cyclopentane,
octahydro 4,7-ethano-1H-indene,
5-methoxy-1-aza-6-oxabicyclo(3.1.0)hexane,
1,1-dimethylcyclohexane,
4-(1-methylethyl)-heptane,
1,4-dimethyl-, -ciscyclohexane,
pentanal,
3-methyl-nonane,
1,2,3-trimethyl-, (1.alpha.,2.beta.,3.alpha.)cyclohexane,
2-beta-pinene,
-Triethylborane,
2,5-dimethyl-, cis-piperazine,
delta-4-carene,
2-methyl-, 2-methylbutyl propanoic acid ester and
3-methyl-pentane;

determining a first mean alveolar gradient for the marker present in the mammal's breath;

comparing the first mean alveolar gradient for the marker present in the mammal's breath to a second mean alveolar gradient for the same marker, found in the breath of a mammal free of lung cancer;

wherein a statistically significant difference in the first mean alveolar gradient from the second mean alveolar gradient indicates the probable presence of lung cancer.

* * * * *